United States Patent [19]
Fletcher et al.

[11] Patent Number: 5,190,539
[45] Date of Patent: Mar. 2, 1993

[54] MICRO-HEAT-PIPE CATHETER

[75] Inventors: Leroy S. Fletcher; George P. Peterson, both of College Station, Tex.

[73] Assignee: Texas A & M University System, College Station, Tex.

[21] Appl. No.: 550,519

[22] Filed: Jul. 10, 1990

[51] Int. Cl.$^5$ ............................................. A61B 17/36
[52] U.S. Cl. ........................................ 606/25; 606/28
[58] Field of Search .................................. 606/21–25, 606/27, 28; 128/401

[56] References Cited

U.S. PATENT DOCUMENTS

| | | | |
|---|---|---|---|
| 3,929,136 | 12/1975 | Kreeb et al. ........................... | 606/25 |
| 4,140,130 | 2/1979 | Storm, III . | |
| 4,206,759 | 6/1980 | Shaw ..................................... | 606/28 |
| 4,476,867 | 10/1984 | Parks . | |
| 4,479,798 | 10/1984 | Parks . | |
| 4,662,383 | 5/1987 | Sogawa et al. . | |
| 4,667,658 | 5/1987 | Guibert . | |
| 4,676,258 | 6/1987 | Inokuchi et al. . | |
| 4,719,919 | 1/1988 | Marchosky et al. . | |
| 4,791,930 | 12/1988 | Suzuki et al. . | |
| 4,819,642 | 4/1989 | Andersen et al. . | |
| 4,825,880 | 5/1989 | Stauffer et al. . | |
| 4,869,247 | 9/1989 | Howard, III et al. . | |
| 4,900,303 | 2/1990 | Lemelson . | |

OTHER PUBLICATIONS

Lele, Local Tumor Hyperthermia in the 1990's Reprinted from: Consensus of Hyperthermia for the 1990's, H. I. Bicker, Ed., Plenum Pub. Corp.
"Encyclopedia of Medical Devices and Instrumentation", J. G. Webster (Ed) John Wiley & Sons, N.Y. Bol. 3:1583 et seq. (1988).
Lele, Ultrasound Hyperthermia, reprinted from "Encyclopedia of Medical Devices and Instrumentation", J. G. Webster (Ed.), John Wiley & Sons, N.Y. vol. 3:1599–1612 (1988).
Waterman et al., Mechanisms of Heat Removal During Local Hyperthermia.
Roizin-Towle, A Concept of Thermal Dose is Urgently Needed For the Clinical Application of Hyperthermia (Letter).
Bicher et al., Local Superficial and Deep Hyperthermia—Factors Affecting Tumor Response and Patient Survival (Meeting Abstract).
Steger et al., Study of Local Interstitial Hyperthermia Induced by Low Power ND:YAG Laser.
Furse et al., Three Dimensional Electromagnetic Power Deposition in Tumors Using Interstitial Antenna Arrays.
Surgery Cryoprobe.

*Primary Examiner*—Lee S. Cohen
*Attorney, Agent, or Firm*—Arnold, White & Durkee

[57] ABSTRACT

A micro-heat-pipe catheter provides a hyperthermia or hypothermia source for the treatment of cancerous tumors or other diseased tissue. The heat-pipe is about the size of a hypodermic needle and is thermally insulated along a substantial portion of its length. The heat-pipe includes a channel, partially charged with an appropriate working fluid. Active or passive heat control tailors the delivery or removal of thermal energy directly to or from the tumor or diseased tissue site.

23 Claims, 2 Drawing Sheets

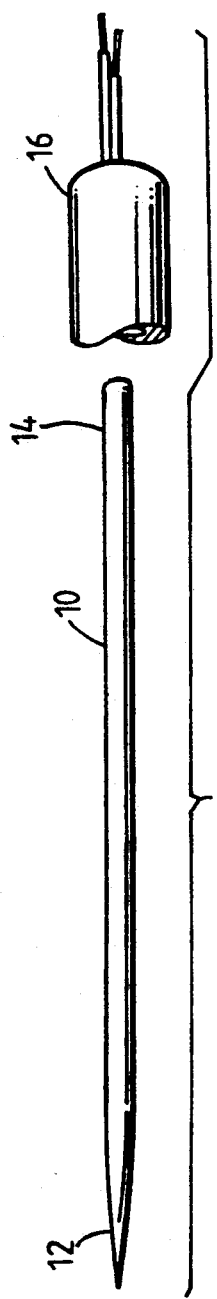
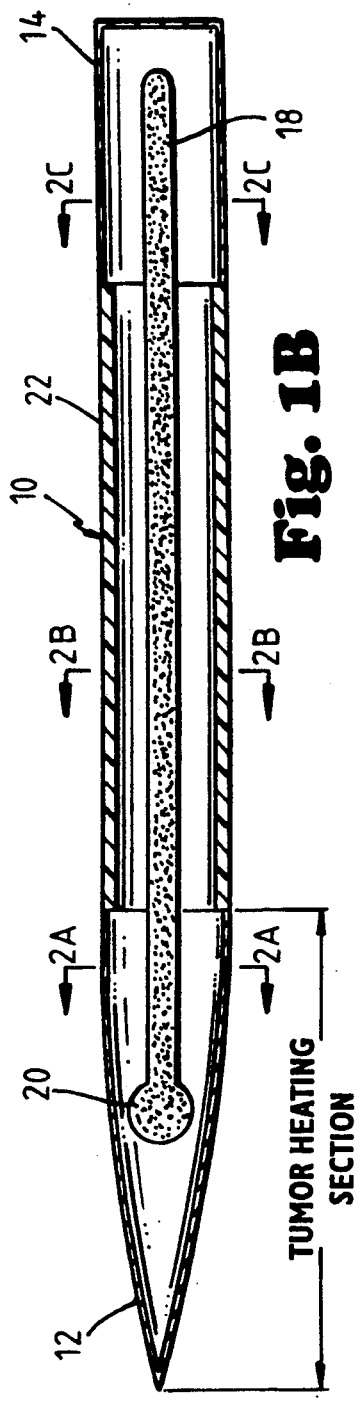
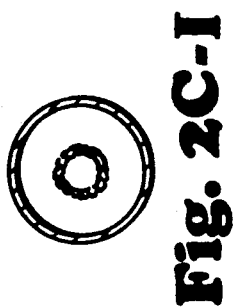
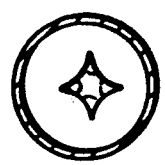

MICRO-HEAT-PIPE CATHETER

SUMMARY OF THE INVENTION

Millions of people are afflicted with some form of cancer every year, and new techniques for cancer treatment are continually being developed. The use of local hyperthermia, or elevating the temperature of a cancerous part of the body to a slightly higher temperature has received increased attention over the past few years. Localized heating of a cancerous tumor (including the edges of the tumor) to therapeutic temperatures of 42.5° C. (108.5° F.) to 43.0° C. (109.4° F.) for periods of 20 to 30 minutes will in most cases destroy the rapidly growing cancer cells and lead to the arrest of tumor growth.

Total body temperatures above 41.8° C. (107.2° F.) are detrimental to the functions of the central nervous system, heart, liver, and kidney, and may even cause histologically obvious damage to tissue cells, whereas tumorcidal effects are generally not observed below 42.5° C. (108.5° F.). At brain temperatures of over 41.8° C. (107.2° F.), the mechanism for regulation of body temperature can be incapacitated and there is danger of 'malignant' or 'runaway' hyperthermia. Further, temperatures of up to 45° C. (113.0° F.) may cause soft tissue necroses and fistulas as well as skin burns. Therefore, accurate temperature control is critical to successful hyperthermia. As a consequence, there is a significant need for development of a simple hyperthermia device which will generate a precisely controllable heat rate that is confined to the tumor region in order to minimize the risk of damage to the surrounding normal tissue and the overall body functions.

Local hyperthermia must elevate the temperature of a cancerous tumor to a therapeutic level while maintaining the temperature of the surrounding tissue at normal levels. Numerous heating methods for tumor treatment have been proposed over the past few decades, and several methods are currently in practice. These heating techniques may be classified from a clinical point of view as non-invasive and invasive.

Non-invasive hyperthermia techniques involve the use of electromagnetic or ultrasound energy focused on the region to be heated by means of external systems. This energy heats the body tissues to the desired temperatures. While it is possible to focus this energy, the resulting effect is regional heating rather than local heating, and the blood flow carries much of the heat away. This approach often exhibits large fluctuations in heating due to variations in blood flow and tissue thermal conductivity.

Both electromagnetic and ultrasound energy must be carefully focused, and the wavelength of the beam must be small compared to the tumor dimensions. As a consequence, microwave heating is not useful for deep tumors, but may be used on diseased areas only a few centimeters into the body. Thus, microwave energy is restricted to superficial tumors or diseased areas not requiring deep penetration. Ultrasound also exhibits a frequency-dependent penetration depth. Bones are very strong absorbers of ultrasound beams while air cavities are almost perfect reflectors. Further, reflections occur at dissimilar tissue interfaces, causing additional problems. Coupling between the applicator and skin also poses a problem in some cases.

Invasive heating techniques include the perfusion of the extremities with extracorporally heated blood, the irrigation of the urinary bladder with heated saline, and other intracavitary methods or interstitial techniques, such as placing heating elements directly into the tumor. The use of interstitial techniques permits the achievement of therapeutic temperature levels without appreciable heating of normal tissues, regardless of the tumor geometry. The use of a number of heating elements permits the regulation of the heat rate to the appropriate level. Interstitial hyperthermia devices include sets of implanted electrodes connected to a radio frequency generator, combinations of implanted and external electrodes, and implanted microwave antennas. Implanted or injected thermoseeds are also considered an invasive heating technique.

Each of these invasive techniques has drawbacks. The use of implanted electrodes, while simple, involves placing an array of needles into the tumor and connecting them to an RF generator. The temperature field for such electrodes is very difficult to control, and the volume that can be heated effectively is rather small, requiring many implants. Such an arrangement may result in non-uniform heating with excessive temperatures. Further, the use of high frequencies and high voltage may interfere with the electronic thermometers and could be harmful to the patient.

Implanted electrodes require connections to an external power source. A large number of connection wires, or coaxial feed lines, may pose major problems. These problems include the over-heating of feed lines, as well as temperature inhomogeneity.

Implanted thermoseeds absorb energy from an externally-applied magnetic induction field. Each acts as a small heating unit, transferring heat to the tumor by conduction. Implanting microwave antennas is probably the most popular invasive heating technique and has been used in many treatments. Generally, an array of seeds or antennas are implanted in the tumor and left in place for the duration of the treatment.

Thermoseeds are generally small cylinders and require careful placement in the tumor because the orientation with respect to the induced magnetic field dictates the degree of tumor heating. As a consequence, each cylinder must be implanted individually. As with other invasive methods, the use of thermoseeds has limited temperature control. Further, areas with poor blood flow may overheat while regions with high blood flow may not attain therapeutic temperatures.

Small ferromagnetic microspheres may be injected into the tumor or into the blood supply. The appropriate region is then subjected to a high intensity, low frequency magnetic field. The microspheres absorb energy from the magnetic field and heat the cancerous tissue by conduction heating. This technique, however, has not been used on humans.

All non-invasive and invasive techniques require a complete knowledge of the temperature distribution in the diseased region. As a consequence, these techniques require the insertion of a large number of invasive temperature probes or an improvement in the thermal modeling of the region between temperature probes.

An ideal heating technique must account for the three-dimensional character of a tumor and its surroundings. Microwave antennas and implanted needle electrodes lack this ability. However, a technique employing a micro-heat-pipe can account for this characteristic.

Micro-heat-pipe technology is well known to those in the field, and small heat-pipes and miniature heat-pipes have been demonstrated to work successfully in the laboratory. Micro groove heat pipes are in development and other types of micro-heat-pipes are available from a variety of commercial micro-heat-pipe manufacturers, such as the Itoh Research and Development Company in Japan.

It would therefore be advantageous to provide a micro-heat-pipe that develops a tightly controlled temperature range in a region restricted to diseased tissue within a body. Such a micro-heat-pipe must deliver a controllable amount of thermal energy to the diseased tissue while minimizing heat transfer to normal tissue surrounding the diseased region. This device should provide localized temperature monitoring and eliminate the use of hazardous electrodes and electromagnetic radiation.

SUMMARY OF THE INVENTION

The present invention provides a controllable heat rate at a tightly controlled constant temperature for use in a micro-heat-pipe charged with an appropriate working fluid to assure a constant temperature operation within the therapeutic temperature range of 42.5° (108.5°) to 43.0° C. (109.4° F.) or whatever temperature range is deemed appropriate for the diseased tissue. The present invention also provides for hypothermia; that is, the removal of thermal energy in appropriate circumstances. This micro-heat-pipe is inserted directly into a tumor or other diseased region of a body and heat is applied to destroy the diseased region. The rate of heat delivered or removed is matched to the thermal conductivity of the tissue and the degree to which the tumor is perfused. The number and depth of such devices to be inserted into a cancerous tumor or diseased tissue depends on the volume and location of the diseased region within the body.

A micro-heat-pipe catheter in accordance with the present invention delivers heat to a tumor or diseased region at constant temperature in a precisely controllable manner without using surgical techniques. The micro-heat-pipe catheter is a simple device that requires no complex external equipment, high voltages, or high radio-frequencies. Further, each catheter may be either actively controlled through a self-contained unit or passively controlled using one of several heat pipe control techniques.

Each catheter may be designed to operate at a specific temperature, and fabricated in different lengths and different diameters for specific tumor locations and volumes. For specific applications, the heat-pipe may be curved to work around an obstruction such as bone or to avoid the invasion of a particular organ. The micro-heat-pipe includes an evaporator or heating section that remains external to the body and a condenser section that is inserted into a tumor or other diseased region of the body. The temperature and heat flux of the heating section of the catheter is controlled to suit individual tumor requirements.

The micro-heat-pipe catheter of the present invention eliminates most of the problems associated with both non-invasive and invasive hyperthermia devices. It is simple to use, easily controlled, and does not require complex supporting facilities. This device eliminates the need for additional temperature control systems and thus minimizes the disturbance of surrounding tissue.

Hyperthermia is generally used in addition to surgery, radiation, and chemotherapy rather than alone as the first line of treatment. Hyperthermia, when used in new or previously treated tumors, is found to have strong antitumor effects. Its efficacy is enhanced remarkably if delivered in conjunction with other cancer therapies. Thus, the micro-heat-pipe catheter of the present invention serves to replace some existing hyperthermia treatment techniques for some cancerous tumors and increases the number of individuals who may be treated. Further, it may be used for some deep seated tumors which cannot be treated with other techniques.

For applications requiring the cooling of the tissue, or hypothermia, the external end of the catheter may be cooled so that the micro heat pipe removes heat from the body.

The catheter is an invasive device; it may be inserted directly into the diseased tissue in a manner similar to a hypodermic needle. A detachable handle may be used for accurate placement, particularly for deep-seated tumors or diseased areas. The handle may be removed and a clip-on heater cap attached to supply the heat to the catheter.

Those of skill in the art will recognize these and other advantages of the present invention while reading the following detailed description in conjunction with the accompanying drawings.

BRIEF DESCRIPTION OF THE DRAWINGS

FIG. 1 is a side view of a micro-heat-pipe catheter.

FIG. 2 is a cutaway view of a micro-heat-pipe catheter, illustrating its internal construction, including cross-sections.

DETAILED DESCRIPTION OF PREFERRED EMBODIMENTS

Figure 3:
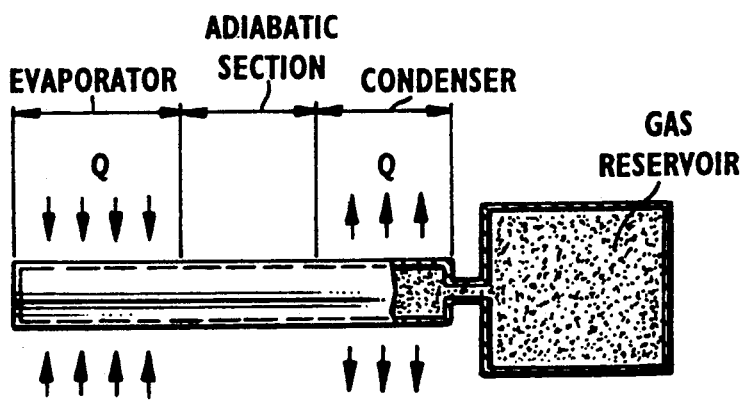
FIG. 3 is a schematic view of a passively controlled gas-loaded heat pipe.

FIG. 1 illustrates a micro-heat-pipe catheter of the present invention. The catheter has a shaft 10, a needle-sharp end 12, and a heat-source end 14. The heat-source end 14 is adapted to fit into a heating element, such as a resistance heater 16, although any highly-controllable heat source or cooling source with temperatures in the appropriate range operate satisfactorily. Such a heat source or cooling source may include a pre-heated or chilled liquid or a cryogenic fluid.

The catheter is to be constructed of stainless steel or other biocompatible material in a manner similar to the construction of hypodermic needles and is to be pointed in a manner similar to hypodermic needles. The heat-source end 14 of the catheter serves as the evaporator end of the heat pipe and the needle-sharp end 12 serves as the condenser end of the heat pipe. In applications requiring the removal of thermal energy, such as hypothermia or the cooling of tissue, the roles of condenser and evaporator are reversed.

The heat-pipe operates on the thermodynamic principal of essentially constant temperature evaporation and condensation. Therefore, the temperature throughout the length of the heat pipe is substantially uniform. The temperature variation between the evaporator and condenser regions in a micro-heat-pipe may be as little as ±0.1° C., depending upon the pressure, temperature, and working fluid used in the heat-pipe.

FIG. 2 illustrates the internal structure of the micro-heat-pipe. As before, the shaft 10 includes a needle-sharp end 12 and a heat-source end 14. The needle-sharp end 12 comprises the tumor-heating section, and this end includes the condenser of the heat pipe. The heat-source end 14 comprises the evaporator.

As shown in FIG. 2, the exterior of the stainless steel shaft 10 of the catheter may be inset by machining and a coating of highly insulating material 22 may be vapor deposited or anodized on the surface so as to minimize the radial heat loss and minimize damage to the normal tissue through which the catheter passes.

The heat pipe includes a channel 18 which has a non-condensible gas reservoir 20. The channel 18 is partially charged with an appropriate working fluid, such as pure water, methanol, ammonia, or nitrogen.

In most two-phase cycles, the presence of non-condensible gases creates a problem due to the partial blockage of the condensing area. Heat pipes are no exception. During normal operation, any non-condensible gases present are carried to the condenser and remain there, reducing the effective condenser surface area. This characteristic, although normally undesirable, can be used to control the direction and amount of heat transfer and/or the condenser temperature (i.e. the temperature at the tumor).

In operation, the working fluid evaporates at the heat-source end 14 and condenses at the tumor-heating section. FIG. 2, in cross-sections C—C, illustrates alternative wicking configurations to carry the condensed working fluid back to the evaporator. Cross section A—A depicts the channel 18 and cross-section B—B depicts the channel 18 and the insulative layer 22.

FIGS. 3 to 6, inclusive, illustrate a number of heat-transfer control techniques. In these figures, the vertical arrows depict the direction of heat transfer.

FIG. 3 illustrates one embodiment of the present invention which may be referred to as a gas-loaded, variable conductance heat pipe. In this type of device, the thermal conductance of the heat pipe varies as a function of the "gas front" position. The term "gas front" refers to the vapor/noncondensible gas interface. As the heat available at the evaporator varies, the vapor temperature varies and the noncondensible gas contained within the reservoir expands or contracts, moving the gas front. This in turn results in a variation in the thermal conductance, i.e. as the heat flux increases, the gas front recedes and the thermal conductance increases due to the larger condenser surface area. In this way, the temperature drop across the evaporator and condenser can be maintained fairly constant even through the evaporator heat flux may fluctuate. This will provide a constant temperature at the tumor site, preventing damage to surrounding tissue.

While in most applications heat pipes operate in a passive manner, adjusting the heat flow rate to compensate for the temperature difference between the evaporator and condenser, several active control schemes have been developed. Most notable among these are: (i) gas-loaded heat pipes with a feedback system, (ii) excess-liquid heat pipes, (iii) vapor flow-modulated heat pipes, and (iv) liquid flow-modulated heat pipes.

Figure 4:
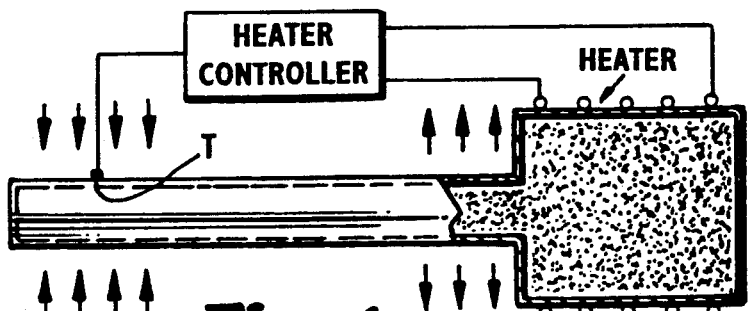
FIG. 4 is a schematic view of an actively controlled gas-loaded heat pipe.

FIG. 4 illustrates an example of an actively-controlled, gas-loaded heat pipe in which the gas volume at the reservoir end sensing device T at the evaporator provides a signal to the reservoir heater. This heater, when activated, can heat the gas contained in the reservoir, causing it to expand and thereby reducing the condenser area.

Figure 5:
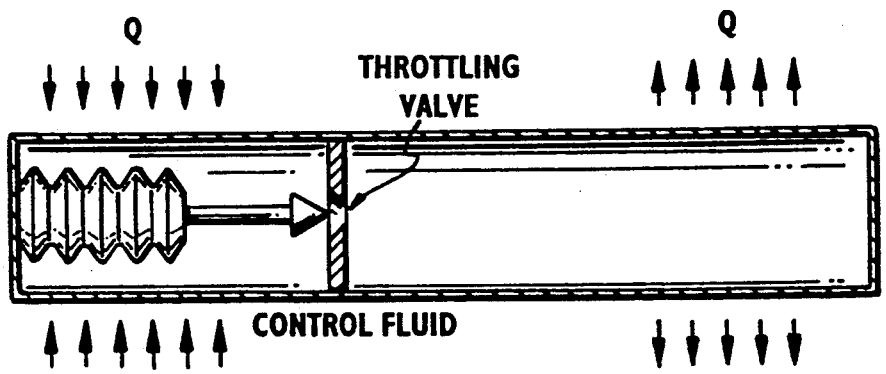
FIG. 5 is a schematic view of a vapor-modulated variable conductance heat pipe.

Excess-liquid heat pipes operate in much the same manner as gas-loaded heat pipes but utilize excess working fluid to block portions of the pipe and control the condenser size or prevent reversal of heat transfer. Vapor-flow-modulated heat pipes utilize a throttling valve to control the amount of vapor leaving the evaporator. FIG. 5 illustrates an example of one such control scheme. Increased evaporator temperatures result in an expansion of the bellows chamber containing the control fluid. This in turn closes down the throttling valve and reduces the flow of vapor to the condenser. This type of device is typically applied in situations where the evaporator temperature varies and a constant condenser temperature is desired.

Figure 6:
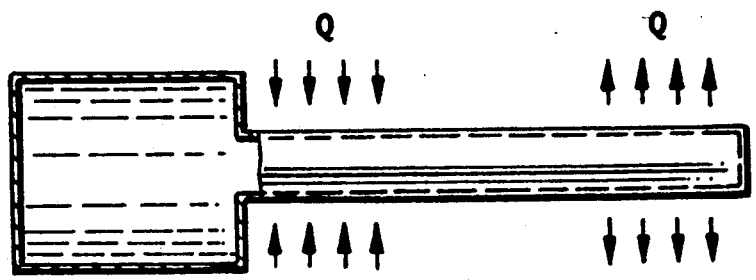
FIG. 6 is a schematic view of a liquid-modulated heat pipe.

FIG. 6 illustrates the principle used in liquid flow-modulated heat pipes. This type of heat pipe has two separate wicking structures, one to transport liquid from the evaporator to the condenser and the other which serves as a liquid trap. As the temperature gradient is reversed, the liquid moves into the trap and starves the evaporator of fluid, again regulating the temperature of the condenser to prevent damage to the surrounding tissue.

Using one of these control techniques, a selection of catheters may be fabricated of different lengths, different materials, different diameters, different temperature and heat rate capabilities, and different lengths of the tumor heating or cooling section of the catheter. Treatment of a cancerous tumor or diseased area may require a number of these micro heat pipe catheters, depending upon the volume, location, and perfusion of the tumor. Also, some micro-heat-pipes may be curved to avoid invasion of normal body organs or to skirt bone material.

The primary feature of the micro heat pipe catheter resides in the heat delivery at a constant temperature within an acceptable temperature range. Such a device eliminates the need for high voltage or high frequency sources, minimizes the need for excessive and complex equipment, provides localized hyperthermia, and protects the patient from possible high voltage or high radiation accidents.

Although various embodiments of the present invention have been described with a certain degree of particularity, it is to be understood that the present disclosure has been made only by way of example. Modifications and changes in details of construction may be made without departing from the spirit and scope of the invention.

We claim:

1. A micro-heat-pipe catheter comprising:
   a. a shaft having a first end and a second end, said first end having a needle-like shape for penetrating soft tissue.
   b. a channel disposed within the shaft, the channel chargeable with a quantity of a working fluid,
   c. an insulating layer disposed along the shaft between the first end and the second end, and
   d. a thermal transfer element thermally coupled to the second end of the shaft.

2. The micro-heat-pipe catheter of claim 1 further comprising a temperature sensor at the second end of the shaft and a controller coupled to the temperature sensor and the thermal transfer element to control the operation of the thermal transfer element.

3. The micro-heat-pipe catheter of claim 1 wherein the shaft is curved.

4. The micro-heat-pipe catheter of claim 1 wherein the thermal transfer element is a resistance heater element.

5. The micro-heat-pipe catheter of claim 1 further comprising a source of pre-heated liquid coupled to the heater element.

6. The micro-heat-pipe catheter of claim 1 wherein the thermal transfer element is a cryogenic element.

7. A micro-heat-pipe catheter comprising:
   a. a shaft having a condenser end and an evaporator end, the condenser end being needle-like in shape,
   b. a channel disposed within the shaft, the channel chargeable with a quantity of a working fluid,
   c. an insulating layer disposed along the shaft between the condenser end and the evaporator end, and
   d. a heater element thermally coupled to the shaft at the evaporator end.

8. The micro-heat-pipe catheter of claim 1 further comprising a temperature sensor at the evaporator end of the shaft and a controller coupled to the temperature sensor and the heater element to control the operation of the heater element.

9. The micro-heat-pipe catheter of claim 1 wherein the shaft is curved.

10. The micro-heat-pipe catheter of claim 1 wherein the heater element is a resistance heater element.

11. The micro-heat-pipe catheter of claim 1 further comprising a source of pre-heated liquid coupled to the heater element.

12. A method of treating a cancerous tumor, comprising the steps of:
   a. charging a quantity of a working fluid within a micro-heat-pipe, the micro-heat-pipe having a condenser end and an evaporator end,
   b. thermally insulating the micro-heat-pipe between the condenser end and the evaporator end,
   c. inserting the condenser end of the micro-heat-pipe into a cancerous tumor, and
   d. heating the evaporator end of the micro-heat-pipe for a predetermined length of time.

13. A micro-heat-pipe catheter comprising:
   a. a shaft having a condenser end and an evaporator end, the condenser end being needle-like in shape and the shaft having an axis,
   b. a channel co-axially disposed within the shaft, the channel chargeable with a quantity of a working fluid, the channel having a condenser end and an evaporator end, the channel further having a non-condensible gas reservoir at the condenser end,
   c. an insulating layer disposed along the shaft between the condenser end and the evaporator end, and
   d. a heater element thermally coupled to the shaft at the evaporator end.

14. The micro-heat-pipe catheter of claim 13 further comprising a temperature sensor at the evaporator end of the shaft and a heater controller coupled to the temperature sensor and the heater element to control the operation of the heater element.

15. A micro-heat-pipe catheter comprising:
   a. a shaft having a condenser end and an evaporator end, the condenser end being needle-like in shape.
   b. a channel disposed within the shaft, the channel chargeable with a quantity of working fluid,
   c. an insulating layer disposed along the shaft between the condenser end and the evaporator end, and
   d. a cooling element thermally coupled to the shaft at the evaporator end.

16. The micro-heat-pipe catheter of claim 15 further comprising a temperature sensor at the evaporator end of the shaft and a controller coupled to the temperature sensor and the cooling element to control the operation of the cooling element.

17. The micro-heat-pipe catheter of claim 15 wherein the shaft is curved.

18. The micro-heat-pipe catheter of claim 15 further comprising a source of chilled liquid coupled to the cooling element.

19. The micro-heat-pipe catheter of claim 9 further comprising a source of cryogenic fluid coupled to the cooling element.

20. A micro-heat-pipe catheter comprising:
   a shaft having a first end, a second end, and an intermediate portion extending therebetween, said first end having a needle-like shape for penetrating soft tissue;
   a channel being disposed within said shaft, said channel being chargeable with a quantity of fluid, and said channel extending between said first end and said second end of said shaft and terminating in a fluid reservoir at said first end;
   a thermal transfer element being coupled to the second end of said shaft; and
   a thermally insulative barrier disposed along said intermediate portion of said shaft, said thermally insulative barrier protecting tissue contacting said intermediate portion of said shaft from damaging temperature change.

21. A method of treating a tumor comprising the steps of:
   inserting a needle-like end of a micro-heat-pipe catheter into said tumor;
   maintaining said needle-like end of said micro-heat-pipe catheter within a prescribed temperature range; and
   thermally insulating a portion of said micro-heat-pipe catheter to protect healthy tissue from thermal damage.

22. The method, as set forth in claim 21, wherein temperature within said prescribed range varies by less than one degree Celsius.

23. The method, as set forth in claim 21, wherein said prescribed temperature range extends from approximately 42.5 degrees Celsius to approximately 43.0 degrees Celsius.

* * * * *

UNITED STATES PATENT AND TRADEMARK OFFICE
CERTIFICATE OF CORRECTION

PATENT NO. : 5,190,539

DATED : March 2, 1993

INVENTOR(S) : Leroy S. Fletcher; George P. Peterson

It is certified that error appears in the above-indentified patent and that said Letters Patent is hereby corrected as shown below:

Column 6, line 57, "." should be --,--.

Column 7, line 21, "1" should be --7--.

Column 7, line 26, "1" should be --7--.

Column 7, line 28, "1" should be --7--.

Column 7, line 30, "1" should be --7--.

Column 8, line 5, "." should be --,--.

Column 8, line 23, "9" should be --15--.

Signed and Sealed this

Twenty-sixth Day of December, 1995

Attest:

BRUCE LEHMAN

Attesting Officer        Commissioner of Patents and Trademarks